United States Patent [19]

Walker et al.

[11] Patent Number: 4,759,759
[45] Date of Patent: Jul. 26, 1988

[54] BUBBLE HEART VALVE

[76] Inventors: David K. Walker, 1576 Cedarglen Rd., Victoria, British Columbia, Canada, V8N 2B2; Richard T. Brownlee, Suite 101, 1780 Fort Street, Victoria, British Columbia, Canada, V8R 1J5; Denton E. Hewgill, 4012 Morningside Close, Victoria, British Columbia, Canada, V8N 3M2; Lawrence N. Scotten, 968 Gorge Road West, Victoria, British Columbia, Canada, V9A 1P1; Roberto G. Racca, 3999 Braefood Road, Victoria, British Columbia, Canada, V8X 2B6

[21] Appl. No.: 564,206

[22] Filed: Dec. 22, 1983

[30] Foreign Application Priority Data

Jun. 23, 1983 [CA] Canada ................................ 431115

[51] Int. Cl.$^4$ .............................................. A61F 2/24
[52] U.S. Cl. ........................................ 623/2; 623/900
[58] Field of Search ................................... 623/2, 900

[56] References Cited

U.S. PATENT DOCUMENTS

| | | | |
|---|---|---|---|
| 3,739,402 | 6/1973 | Cooley et al. | 623/900 X |
| 4,222,126 | 9/1980 | Boretos et al. | 623/2 |
| 4,340,977 | 7/1982 | Brownlee et al. | 623/2 |
| 4,490,859 | 1/1985 | Black et al. | 623/2 |
| 4,605,407 | 8/1986 | Black et al. | 623/2 |

*Primary Examiner*—Ronald L. Frinks

*Attorney, Agent, or Firm*—Birch, Stewart, Kolasch & Birch

[57] ABSTRACT

A novel bileaflet mitral heart valve is provided herein, which in two alternative embodiments may have symmetrical leaflets or assymmetrical leaflets. It has a stent including a circular base and a pair of upstanding struts separating a pair of arcuately shaped, depressed, reliefs, each such relief being bounded by a smooth curve interconnecting the struts to the circular base. A flexible, durable, biocompatible, e.g. a pericardial, covering is secured to the stent and provides two opposed molded, flexible, flappably-movable, valve leaflets secured along the smooth curve defining the upper perimeter of the reliefs. These valve leaflets each are preformed and molded so that the free margin of the valve leaflets along the free edge of each of the leaflets between the tips of the struts is related to the circumference of the circular base such that, when the valve is in the open position, the cross-sectional area is substantially equal to the inside cross-sectional area of the circular base, and when the valve is in its relaxed and natural position, the free edges of the leaflets drop down and sealingy meet in substantially wrinkle-free form at a curve of apposition, preferably in the plane defined by the tip of the struts and the axis of the valve to provide symmetrical leaflets, and, in one embodiment, may follow the approximate shape of a catenary curve. The two leaflets may thus approach the configuration of the natural human mitral valve and the shape of the leaflets in that closed position approximate that of a surface formed by two coapting bubbles under pressure.

29 Claims, 8 Drawing Sheets

BUBBLE HEART VALVE

BACKGROUND OF THE INVENTION (i) Field of the Invention

This invention relates to a replacement heart valve and particularly to a two leaflet replacement heart valve.

(ii) Description of the Prior Art

The human heart has four valves which when properly functioning allow unidirectional blood flow. Heart valve disease in advanced forms causes severe disability or death. The quality and length of life for patients suffering from valve disease can be remarkably improved by surgical treatment, which usually involves the total replacement of the diseased valve with a prosthetic valve. When natural valves malfunction they can be replaced, by a variety of prosthetic heart valves, in order to restore effective blood flow.

Since the first successful implantation in a human, nearly 50 different valve types have been introduced and many have been discarded; of those remaining, two basic types are in use—those with occluders constructed of human or animal tissues (tissue valves) and those with occluders constructed of various metals, carbon, and plastic components (nontissue or mechanical valves). These devices have come in various forms of flexible unicusp, bicuspid, and tricuspid valves, ball valves and "butterfly" or flapper valves. The mechanical valves have one or more rigid occluders, e.g. discs or balls which slide or tilt in a framework, and are generally made of titanium or hardened graphite. Tissue valves were developed in an attempt to eliminate some of the problems, e.g., noisy operation and a tendency to cause blood clotting, which arose with all of the mechanical valves. Flexible leaflets for tissue valves are usually made of chemically denatured biological tissues, e.g. whole porcine aortic valves and bovine pericardium. The mechanical valves require lifelong use of anticoagulants by the patient, and the long-term durability of the tissue valves is in question. It is believed that a mitral prosthesis which anatomically resembles the natural bileaflet valve is more likely to produce and take advantage of physiologic ventricular flow patterns which appear to be associated with efficient natural valve closure. However, the extent to which these flow patterns aid in the closure of the mitral valve is still undetermined. Also, from a surgical point of view, a mitral valve having only two struts projecting into the ventricle may in some cases be suitable for implantation where the use of a three leaflet valve would be difficult. At present, the only flexible occluder prostheses commercially available are those having three leaflets.

Significant late complications following implantation of these valves can occur and are related to valve design and materials. Present valve replacements do not permit restoration of normal pressure-flow dynamics at all levels of cardiac function. Thus, there is still no clear-cut choice for the surgeon of what valve to use and the search for the ideal replacement valve is continuing.

Stented tissue valves, that is, frame supported valvular grafts which may be either xenografts (heterografts) or allografts (homografts), have been used as replacement heart valves. (See, for example, Carpentier et al., J. Thorac. Cardiovasc, Surg. 68: 771 (1974); Zuhdi et al., Ann. Thorac. Surg. 17: 479 (1974); Horowitz et al., J. Thorac. Cardiovasc. Surg. 767: 885 (1974). In general, such grafts have been mounted on supporting frames (stents) which provide rigid orifice rings (see Weldon et al., J. Surg. Research 6: 548 (1966). Some stents have included struts capable of flexing inwardly to a limited extent, thereby reducing stresses imposed on the valve leaflets and decreasing possible erosion of surrounding cardiac tissues of the patient (see Sugie et al., J. Thorac. Cardiobasc. Surg. 57: 455 (1969); and Hardy, Human Organ Support and Replacement, 338 et. seq.). Despite the encouraging results with prosthetic tissue heart valves and in contrast to non-tissue prosthetic valves, there is a continuing need for improvement, particularly with regard to the hydrodynamic performance and long-range durability of the tissue valves.

The art is still faced with the desirability of providing an improved stent for a tissue (xenograft or allograft) heart valve which is capable of yielding to a limited extent in response to forces which tend to alter the configuration and circumference of the orifice ring, thereby improving the hydrodynamics and long term reliability of the valves. Accordingly, continued efforts are being made to develop more efficient, reliable and biocompatible prostheses.

Several investigators have studied the stresses to which natural and prosthetic valve leaflets are exposed in an attempt to improve the longterm structural integrity of leaflet valves. One investigator has provided a synthetic trileaflet aortic valve prosthesis. A seamless leaflet valve has been developed by another investigator and this valve has been provided with geometry designed to reduce shear stress at the commissures. There are few flexible leaflet prostheses made specifically for the mitral position. The search for improved devices continues because present valve designs can limit patient activity and can produce significant late complications.

The results of such continued efforts are evidenced in heart valves which are disclosed in issued United States patents.

U.S. Pat. No. 2,832,078 issued Apr. 29, 1958 to D. T. Williams discloses an aortic heart valve including a slotted cylindrical sheel with an internal three-sac membrane to provide opening and closing ports, which seal at the centre of the cylindrical shell.

U.S. Pat. No. 3,197,788 issued Aug. 3, 1965 to F. J. Segger provides an aortic heart valve including a deformable cone-shaped cusp-supporting ring, with the cusps having smooth curved surfaces.

U.S. Pat. No. 3,548,418 issued Dec. 22, 1970 to W. W. Angell et al. provides a graft-supporting ring for grafting porcine aortic valves in which the ring is generally in the form of the residual portion of a conical shell, having three struts, the ring being completely covered and having three internal depressed valve cusps.

U.S. Pat. No. 3,570,014 issued Mar. 16, 1971 to W. D. Hancock provides a stent for aortic and mitral heart valves in which the stent includes a ring and three support arms rising therefrom, to which commissures and cusps of a heart valve are attached.

U.S. Pat. No. 3,714,671 issued Feb. 6, 1973 to W. S. Edwards et al. provides a stent for supporting a tricuspid heart valve, in which the ring comprises portions of ellipses, in which the upstanding portions are covered with fabric and which terminate in radial wings, and to which three valve cusps are sutured, the valve cusps having straight trimmed edges, and being supported without tension.

U.S. Pat. No. 3,736,598 issued June 5, 1973 to B. J. Bellhouse et al. provides an aortic valve including a ring having three legs folded to U-shaped sections to which are attached three valve cusps whose free edges meet in radial planes of abutment.

U.S. Pat. No. 3,739,402 issued June 19, 1973 to D.A. Cooley et al. provides a graft support for a bicusp valve which includes a frusto-conical ring and a pair of inverted frusto-conical segments defining struts, all provided with a fabric cover, to which are secured a pair of cusps whose upper edges lie adjacent to each other to form the valve opening.

U.S. Pat. No. 3,733,062 issued July 10, 1973 to V. Parsonnet provides a heart valve construction including a stent having three lower arcuate portions and three upstanding posts, to which a fabric sheath is secured, and from which three valve leaflets, each having an arcuate edge and a straight edge are secured, so that the straight edges provide an upper meeting closure.

U.S. Pat. No. 3,755,823 issued Sept. 4, 1973 to W. D. Hancock provides a stent for heart valves in the form of a flexible stent including a ring having three spaced-apart apexes to which a cloth sleeve is attached and to which three valve cusps are attached, so that the free edges sag towards the centre, at which point they meet at a central, slightly raised point. This valve utilizes a whole porcine aortic valve which is pretreated before mounting on the stent.

U.S. Pat. No. 3,938,197 issued Feb. 17, 1976 to S. Milo provides a heart valve including a ring to which are attached a plurality of flat valve flaps whose free edges all meet in abutting relation.

U.S. Pat. No. 3,983,581 issued Oct. 5, 1976 to W. W. Angell et al. provides a heart valve stent of a particular shape, to which a covering is attached, and from which three valve cusps are attached so that their free edges meet at three commissures, and so that their common points meet at a central depression. A whole porcine xenograft is mounted to the stent.

U.S. Pat. No. 4,035,849 issued July 19, 1977 to W. W. Angell et al. provides a heart valve stent of a particular shape, to which a covering having a bead along its perimeter is attached and from which three valve cusps are attached, so that their free edges meet at three commissures and so that their common points meet at a central depression. A whole porcine xenograft is mounted to the stent.

U.S. Pat. No. 4,084,268 issued Apr. 18, 1978 to M. I. Ionescu et al. provides a heart valve including a dish-shaped cloth-covered stent having three upright posts, to which three cusps are attached, the cusps meeting at their upper edges at a flat closed portion, and in which the knots of the stitches are covered by a pledget and cover. This valve uses pretreated bovine pericardium for its three leaflets.

U.S. Pat. No. 4,106,129 issued Aug. 15, 1978 to A. F. Carpentier et al. provides a heart valve including a deformable wireframe stent having three inverted U-shaped commissure supports, to which are secured a cover, and from which are suspended three valve leaflets meeting along the commissures. A whole porcine xenograft is mounted to the stent.

U.S. Pat. No. 4,164,046 issued Aug. 14, 1979 to D. A. Cooley provides a mitral or tricuspid valve replacement which is based on an open ring stent.

U.S. Pat. No. 4,172,295 issued Oct. 30, 1979 to R. J. Batter provides a tricuspid heart valve dish-shaped cloth-covered stent having three upright ports to which are attached three cusps meeting at their upper edges at a flat closed position, in which the knots of the stitches are covered by a pledget and cover, and in which securing holes are provided between the cusps.

U.S. Pat. No. 4,178,639 issued Dec. 18, 1979 to J. C. Bokros provides a heart valve having an annular valve body and a pair of pivotally secured valve leaflets.

U.S. Pat. No. 3,739,402, to Cooley shows a stent which is a ring generally oblong in form and having a pair of projecting struts either extending perpendicular to the ring or outwardly inclined. The stent is covered with a fabric cover. The covered stent supports a pair of cusps defined by a tubular tissue covering around the struts and intervening space. The cusps, when the valve is in its closed position, follows a horizontal path between the struts.

U.S. Pat. No. 3,608,097 to Bellhouse et al discloses a tubular valve having at least three cusp-like pliable elements. The cusps are space 120° apart and, when opened, form a cylindrical opening.

U.S. Pat. No. 4,222,126 to Boreless et al discloses a three leaflet heart valve with a semi-rigid frame of a bore ring and three struts and an integral elastomeric membrane which provides the three leaflets. The transition between the frame and the leaflet is tapered.

U.S. Pat. No. 4,275,469 patented June 30, 1981 by S. Gabbay provided a novel prosthetic heart valve. The valve included a tubular membrane having a flexible generally circular inlet end adapted to be attached to the annulus of a heart. One side of the tube was held to the heart cavity as by attachment to the papillary muscle. The other side of the tube was formed as an extended single flap adapted to move toward and away from the membrane on the attached side. This provided a closed or open valve at the outlet end.

Another valve structure was disclosed at the ESAO Proceedings at Brussels, Belgium, Sept. 1–3, 1982 in a paper by M. M. Black et al. That paper refers to Black et al United Kingdom Patent Application No. 8,201,793, which provides a bicuspid bioprosthetic mitral heart valve including a pair of leaflets secured to a valve base whose ring thickness varies to provide differential flexibility in the plane of the valve base, and to valve ports. The leaflet is cut from a flat sheet of fully fixed tissue originating from a conical solid having only one axis of curvature. The valve leaflet is derived from a conical surface that can buckle from one stable geometry to another so that when the two leaflets buckle inwards and their free edges coapt, a closed valve configuration obtains.

U.S. Pat. No. 4,340,977 of Richard T. Brownlee et al, provided a stented mitral heart valve which overcame many of the deficiencies of the prior art heart valves. This mitral heart valve had stent including a circular base and a pair of diametrically opposed struts, separating a pair of diametrically opposed, arcuately shaped, depressed reliefs, each such relief being bounded by a smooth curve interconnecting the struts to the circular base; a flexible, durable biocompatible covering secured to the stent and providing two equal, opposed, molded, flappably-movable, valve leaflets secured along the smooth curve defining the upper perimeter of the reliefs; the valve leaflets each being preformed and molded so that the free margins of the biocompatible covering along the free edge of each of the leaflets between the tips of each associated strut is so related to the circumference of the circular base, that when the valve is in its open position, the cross-sectional area of the exit is substantially equal to the cross-sectional area of the inside of the circular base, and, when the valve is in its relaxed and natural closed position, the shape of the leaflets is such that the free edges of the leaflets drop down and sealingly meet in substantially wrinkle-free form at a curve of apposition in the plane defined by the tips of the struts and the axis of the valve, and flow the approximate shape of a catenary curve.

Nevertheless even that mitral valve has not solved all the problems.

SUMMARY OF THE INVENTION (i) Aims of the Invention

In spite of all these prior patents, improvements are still required to provide valves which: provide minimal obstruction to the forward flow of blood and minimal reflux of blood during closure and when closed; result in a minimum amount of concentrated mechanical stress and strain to the valve which would materially contribute to shortening the life of the valve; provide adequate support for attachment within the heart; minimize haemolysis and thrombosisp do not create significant turbulence in the blood stream in both systole and diastole, which can damage blood elements; provide free flow central orifice configuration; provide rapid opening and closing; have potential minimal compressive and tensile stress distribution; have high ratio of available valve flow area to tissue annulus area (i.e. area of the opening in the heart muscle); provide minimal obstruction to the left ventricular outflow tract; provide negligible retrograde flow; provide maximal conformity to the normal anatomic valve configuration; provide minimal thromboembolic (blood clotting) potential; provide silent operation; have improved reliability by minimizing stresses in the flexing cusps tissue; and incorporate flexibility and deformability in their functional operation.

A valve significantly better than present devices would have superior hydrodynamic performance, would not require the use of anticoagulants, would not limit patient activity and in the case of a leaflet valve would have long term durability.

Accordingly, a broad object of this invention is to provide an improved valve for use for heart valve replacements.

Further objectives of this invention are to provide heart valves having the following desirable characteristics:

1. free flow central orifice configuration;
2. rapid opening and closing;
3. potential minimal compressive and tensile stress distribution on flexing leaflets and hence improved valve reliability;
4. high ratio of available valve flow area to implant site area;
5. relative ease of fabrication of all sizes compared to other tissue type valves;
6. minimal obstruction to the left ventricular outflow tract;
7. negligible retrograde flow;
8. maximal conformity to the natural anatomic valve configuration;
9. minimal thromboembolic potential;
10. ease of handling and insertion; and
11. silent operation.

(ii) Statements of Invention

The present invention proposes to provide a flexible two leaflet replacement heart valve which would have significant advantages particularly in the mitral position. The closed leaflets would have a uniform stress distribution assuming uniform mechanical properties in the leaflet material. This is a desirable condition for increasing the durability of the valve by minimizing tensile stress concentrations in the closed leaflets.

The present invention also proposes to provide a valve which offers minimal obstruction to flow when fully open. Any obstruction to flow other than that necessary for anchoring the prosthesis to the implantation site is undesirable because it will result in additional transalvular energy loss and blood cell trauma.

In general terms, by the present invention, a two leaflet replacement heart valve has been developed in which the shape of the leaflets in the closed position approximates that of the surface formed by two coapting symmetrical bubbles under pressure.

By one embodiment of this invention, a mitral heart valve is provided comprising: a stent including a circular base and a pair of upstanding struts separating a pair of arcuately shaped, depressed reliefs each such relief being bounded by a smooth curve interconnecting the struts to the circular base; a flexible, durable, biocompatible covering secured to the stents and providing two opposed, molded, flexible, flappable-movable valve leaflets secured along the smooth curve defining the upper perimeter of the reliefs; the valve leaflets each being preformed and molded so that the free margin of the valve leaflets along the free edge of each of the leaflets between the tips of the struts is related to the circumference of the circular base such that, when the valve is in the open position, the cross-sectional area is substantially equal to the cross-sectional area of the inside of the circular base, and when the valve is in its relaxed and natural closed position, the free edges of the leaflets drop down and sealingly meet in substantially wrinkle-free form at a curve of apposition, the shape of the leaflets in that closed position approximating that of a surface formed by two coapting bubbles under, the shape of said surface formed by said two coapting bubbles under pressure being defined by the following five simultaneous equations:

$$S(u) = 2\int_D\int \sqrt{1 + u_x^2 + u_y^2}\, dx\, dy + \oint_{\partial D} u(x,y)\, d\sigma \tag{1}$$

$$I(u) = 2\int_D\int \sqrt{1 + u_x^2 + u_y^2}\, dx\, dy + \oint_D u(x,y)\, d\sigma + \lambda \int_D\int u(x,y)\, dx\, dy \tag{2}$$

$$\frac{\partial}{\partial x}\left[\frac{u_x}{\sqrt{1 + u_x^2 + u_y^2}}\right] + \frac{\partial}{\partial y}\left[\frac{u_y}{\sqrt{1 + u_x^2 + u_y^2}}\right] = 2\lambda \tag{3}$$

$$3 u_y^2 = 1 + u_x^2 \text{ at } x = 0. \tag{4}$$

$$u(x,y) = x \sin\alpha \quad x,y \in D. \tag{5}$$

wherein:

$$u_x = \partial \frac{du}{dx} \text{ ; and } u_y = \partial \frac{du}{dy} \text{ ;}$$

$\alpha$ is the angle between the plane containing the stent boundry and x-y plane; and D is an ellipse having a short side "a" and a long side "b" formed as a projection of the stent boundry in the x-y plane.

(iii) Other Features of the Invention

By a preferred embodiment of this invention, the curve of apposition is in the plane defined by the tip of the struts and the axis of the valve.

By two features of these embodiments of this invention, the valve leaflets may comprise two equal, identical, opposed, moulded, flexible, flappably-movable valve leaflets, or may comprise two unequal, opposed, moulded, flexible, flappably-movable valve leaflets.

By another feature of these embodiments, the free edges of the leaflets meet at a curve which follows the shape of a catenary.

By a preferred feature of these embodiments of this invention, the above five equations may be solved by computational techniques by discretizing the equations and solving by a numerical technique by dividing the ellipse into four pieces, forming a grid on half of D, discretizing the partial derivatives by second order finite difference approximations and solving the resulting non-linear algebraic equations by successive non-linear overrelaxation.

By another feature of these embodiments, the struts are substantially identical.

By yet another feature of these embodiments, the reliefs are symmetrically disposed equidistant from the struts.

By a still further feature of these embodiments, the reliefs are asymmetrically disposed with respect to the struts.

By a still further feature of these embodiments, the valve leaflets are formed of pericardium treated with glytaraldehyde.

By yet a further feature of these embodiments, the leaflets of pericardium are secured to each other and to the struts by sutures.

By still a further feature of these embodiments, the struts lie within the surface of a cone having the circular stent base as the conic base.

By yet a further feature of these embodiments, the smooth curve interconnecting the struts is a parabola.

By another feature of these embodiments, the stent is formed of a flexible, elastically deformable material, so that the struts may flex slightly.

By a further feature of these embodiments, the material is polypropylene or an acetal copolymer.

By yet a further feature of these embodiments, the valve leaflets are formed of bovine, porcine or human fascia lata or dura mater, or of polyurethane.

BRIEF DESCRIPTION OF THE DRAWINGS

In the accompanying drawings,

FIG. 5 is a view of the schematic geometry of a symmetric bileaflet valve, in which

FIG. 6 is a view of the schematic geometry of an asymmetric bileaflet valve in which

DESCRIPTION OF PREFERRED EMBODIMENTS (i) Generalized Description of the Invention with Reference to FIGS. 1-3, 5 and 6

Figure 4:
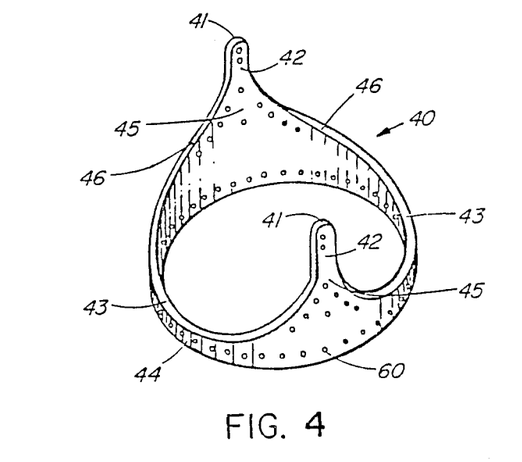
FIGS. 4 is a perspective view of a valve stent.
Figure 5A:
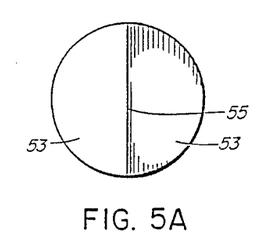
FIG. 5A is a top plan view.
Figure 5B:
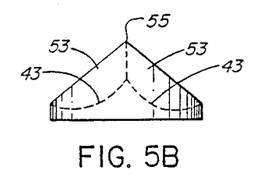
FIG. 5B is a front elevational view and FIG. 5C is a side elevational view.
Figure 5C:
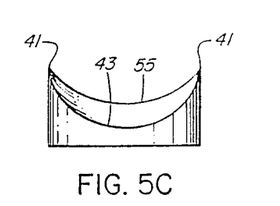
Figure 6A:
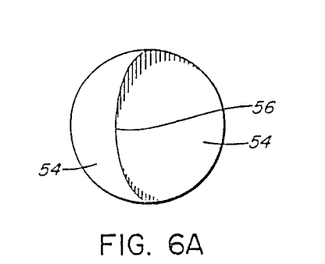
FIG. 6A is a top plan view.
Figure 6B:
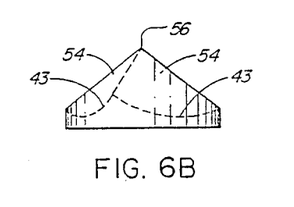
FIG. 6B is a front elevational view and FIG. 6C is a side elevational view.
Figure 6C:
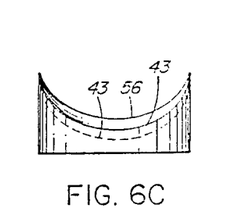

The leaflets of the valve in the closed position were designed to take the shape of two coapting bubbles under pressure which would form on a stent which is shown in FIG. 4. The shape of the bubble surfaces was computed given the stent boundary and the length of the curve or line where the two bubble surfaces meet, according to the following computational technique. Given the boundary of the stent and the length of the curve line where the bubbles meet, a computer program was developed to compute the shape of the bubbles which would be formed over the stent. The length of the curve or line where the bubbles meet was to be computed to be equal to half the base circumference of the stent. In this way, the valve in the open position would have an exit orifice area equal to that of the entrance orifice to the valve. This design would then exhibit minimum possible obstruction to flow. Iteration of the computer program was continued until the desired length where the bubbles meet was obtained.

For the symmetric leaflet valve, the leaflets were designed to take the shape of two coapting symmetric bubbles under pressure and, where the two bubble surfaces meet is a line (as seen in FIG. 5). For the asymmetric leaflet valve, the leaflets were designed to take the shape of two coapting asymmetric bubbles under pressure, and, where the two bubbles meet is a curve (as seen in FIG. 6).

The following mathematic discussion pertains to the design of the symmetric leaflets.

A bubble, or a minimal surface, has the property that it minimizes its total surface area while satisfying certain constraints. A bubble, unlike a sheet of rubber, cannot transmit shear stress and thus forms a surface which has constant stress throughout. This uniform stress was the main reason for choosing a minimal surface as the shape of the leaflets in the closed position.

Figure 1:
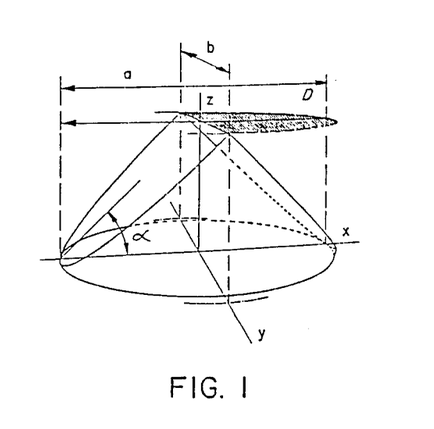
FIG. 1 is a depiction of the coordinate system used for computation of the bubble surface.

The stent boundary was defined as shown in FIG. 1. The projection of the stent boundary on the x-y plane was idealized as an ellipse with short side "a" and long side "b". The angle between the plane containing the stent boundary and the x-y plane was $\alpha$. The bubble was forced to be symmetrical by computing only over half of the ellipse (D).

If u(x, y) is the function which represents the surface, then the surface area of the bubble is:

$$S(u) = 2 \int \int_D \sqrt{1 + u_x^2 + u_y^2} \, dxdy + \int_{\partial D} u(x,y) d\sigma \quad (1)$$

where the first integral represents the area of the curved surface, and the second represents the area of the flat sheet formed between the two bubbles. Next a Lagrange multiplier term is added to impose a constraint that the bubble encloses a fixed volume. Thus, the full functional is:

$$I(u) = 2 \int \int_D \sqrt{1 + u_x^2 + u_y^2} \, dxdy + \int_D u(x,y) d\sigma + \lambda \int \int_D u(x,y) dxdy \quad (2)$$

The partial differential equation for the surface is the EulerLagrange equation for a stationary I, that is:

$$\frac{\partial}{\partial x} \left[ \frac{u_x}{\sqrt{1 + u_x^2 + u_y^2}} \right] + \frac{\partial}{\partial y} \left[ \frac{u_y}{\sqrt{1 + u_x^2 + u_y^2}} \right] = 2\lambda \quad (3)$$

The parameter $\lambda$ turns out to be the mean curvature for the surface. If $\lambda = 0$, then the surface has no internal pressure.

Next, the boundary condition for the boundary where the two curved sheets meet the centre planar sheet is determined. The divergence theorem gives this as the natural boundary condition:

$$3u_y^2 = 1 + u_x^2 \quad \text{at } x=0, \quad (4)$$

Finally, the boundary condition for the stent is:

$$u(x,y) = x \sin\alpha \quad x,y \in D, \quad (5)$$

where $$u_x = \partial \frac{du}{dx} \text{ and } u_y = \partial \frac{du}{dy}.$$

These equations form the complete definition of the surface. A solution to the equations does not exist for all a, b, $\lambda$ and $\alpha$. These parameters all interact as a bubble cannot be formed which curves too tightly and yet fits a large stent.

As a mathematical solution to these equations is not available, the equations were discretized and were solved by numerical techniques. To do this, the ellipse was divided into four pieces and a grid was formed on half of D. The partial derivatives in the equations were discretized by second order finite difference approximations, and the resulting non-linear algebraic equations were solved by successive non-linear overrelaxation. The relaxation required 500 passes to give an error of 0.1% (one quarter of the surface and a 25×25 grid). The error was computed by directly computing the mean curvature of the final answer.

The mean curvature parameter $\lambda$ was guessed by a shooting method. If $\lambda$ is too large then the surface will fail to exist, and if $\lambda=0$ then it will be planar for this model. The length of the curve where the two bubbles intersect determines the open size of the valve. The length can be adjusted (within limits imposed by a, b, and $\alpha$) by experimentally adjusting $\lambda$, computing the surface, and then computing the length from the resulting surface.

Figure 2:
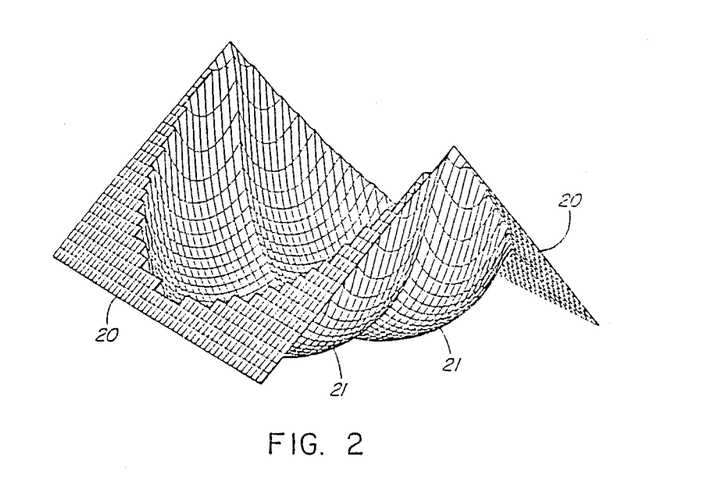
FIG. 2 is a three dimensional perspective view of symmetric leaflet surfaces.

FIG. 2 shows a three dimensional perspective plot of the minimal surface for symmetrical leaflets. The planar parts 20 represent the plane formed on the stent, while the curved portions 21 represent the leaflets having the shape of two coapting bubbles. The figure shows the normal closed position of the valve.

Figure 3:
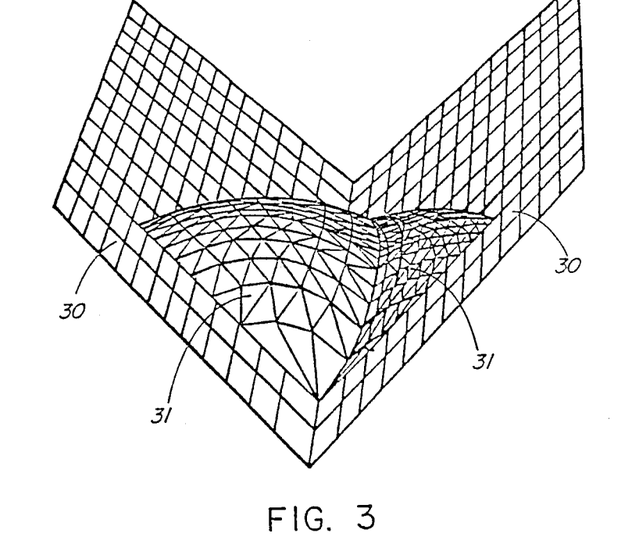
FIG. 3 is a three dimensional perspective view of asymmetric leaflet surfaces.

The leaflets of th asymmetrical valve were designed after the shape of two nonidentical coapting bubbles formed on the valve stent. The bubble surfaces were computed using an enhanced version of the algorithm outlined above, in which the condition of symmetry is no longer required. A typical three dimensional perspective plot of a surface generated by the program is shown in FIG. 3, in which the planar parts 30 again represent the plane formed on the stent, and in which the curved portions 31 represent the leaflets having the shape of two coapting bubbles.

The use of a computer program eliminates the need for tedious measurements and allows fast determination of leaflet shape for different stent configurations. Additionally, the computational technique allows simulation of boundary conditions which can not be realised with a bubble but which may occur in the case of tissue leaflets. In particular, there is a fundamental difference between two bubble surfaces joining and two tissue leaflets coapting. In the first case, the surface formed where the bubbles join has the thickness of the bubble film. For tissue leaflets, the thickness where they coapt becomes twice that of a single leaflet. Also, the computational technique allowed variation of the amount of tissue overlap where the leaflets coapted.

(ii) Description of FIG. 4

As seen in FIG. 4, the stent 40 is symmetrical about the plane through the axis of the valve and the tip 41 of the stent posts 42 and includes diametrically opposed reliefs 43 which may, if desired, be slightly splayed from the vertical axis of the valve to allow for tissue anchoring at the valve outlet without causing obstruction to flow with the valve fully open. The stent 40 also includes a low cylindrical base member or ring 44. Disposed about the cylindrical base member or ring 44 are a pair of identical, diametrically opposed struts 45 between which are the pair of identical, diametrically opposed reliefs 43. The struts can, of course be not precisely true conical segments but may be within virtually cylindrical surfaces and still provide a stent 40 which can be used in providing the nitral valve replacement of an embodiment of this invention.

The stent 40 is made as light and unbulky as is compatible with the needed strength and with avoidance of sharp edges. Preferably it is made of a flexible, elastically-deformable material, e.g., synthetic plastic materials, e.g. polypropylene or acetal copolymer, so that the struts 45 may flex slightly. The struts 45 have rounded extremities or tips 41 and are connected to the cylindrical base member or ring 44 by smooth curves 46 to give reliefs 43 an arcuate shape.

Figure 9:
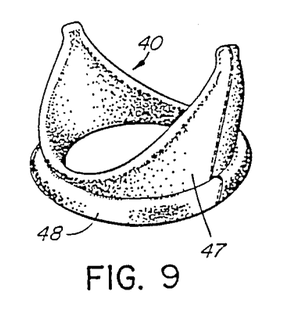
FIG. 9 is a perspective view of a covered stent forming part of both the symmetric and asymmetric leaflet valve replacement of one embodiment of this invention.

(iii) Description of FIG. 9

As shown in FIG. 9, the stent 10 has a durable flexible biocompatible covering 47 terminating in a padded suturing ring 48 at the base. The covering increases the biocompatibility of the valve and reduces leaflet wear along the hinge lines. The suturing ring 48 was stitched to the stent 40 along the bottom edge.

(iv) Description of FIGS. 7, 8, 10, 11, 12 and 13

Figure 7:
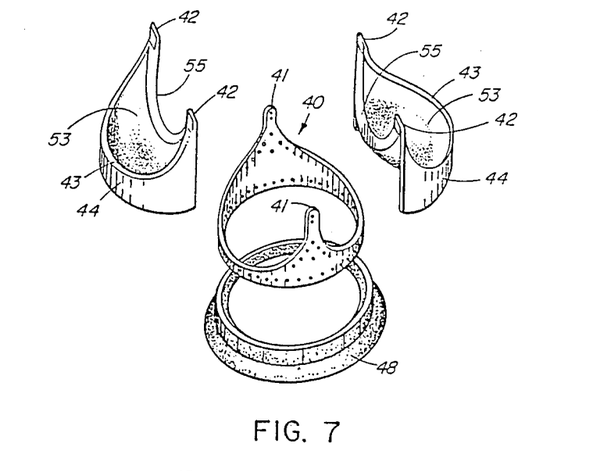
FIG. 7 is an exploded perspective view of the assembly of a symmetric bileaflet valve.
Figure 8:
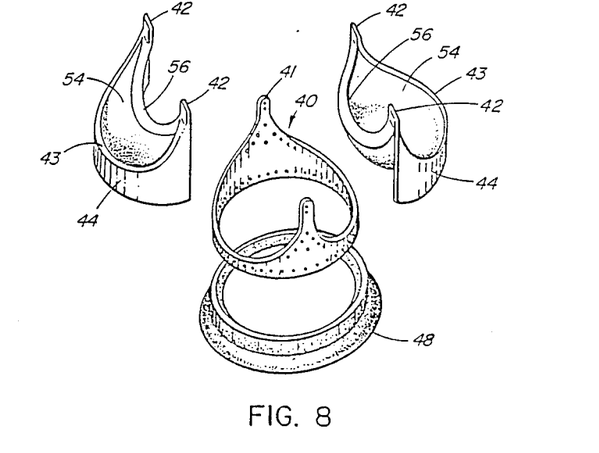
FIG. 8 is an exploded perspective view of the assembly of an asymmetric bileaflet valve.
Figure 10:
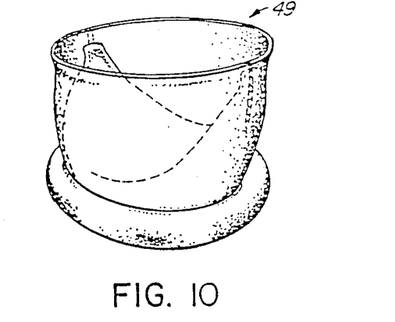
FIG. 10 is a perspective view of the symmetric mitral valve of one embodiment of this invention, in the open configuration.
Figure 11:
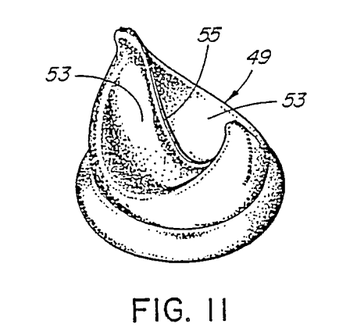
FIG. 11 is a perspective view of the symmetric mitral valve of one embodiment of this invention in the closed configuration.
Figure 12:
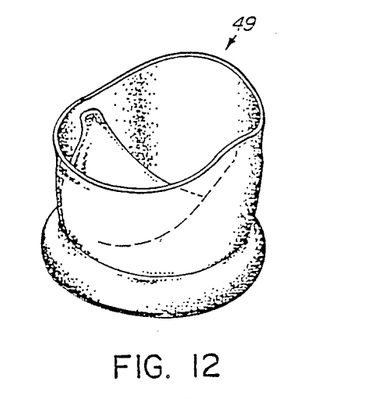
FIG. 12 is a perspective view of the asymmetric mitral valve of one embodiment of this invention, in the open configuration.
Figure 13:
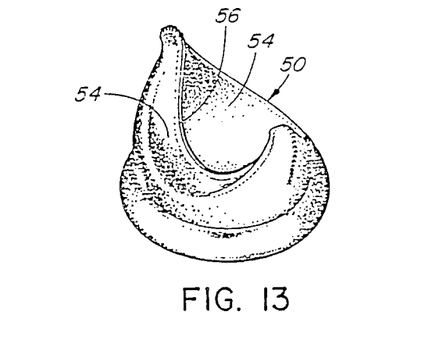
FIG. 13 is a perspective view of the asymmetric mitral valve of one embodiment of this invention in the closed configuration.

The symmetric leaflet mitral valve 49 of FIGS. 10 and 11, and the asymmetric leaflet mitral valve 50 of FIGS. 12 and 13 are shown in exploded form in FIGS. 7 and 8 respectively. For the sake of clarity, the flexible durable biocompatible covering 47 on the stent is not shown either in FIG. 7 or in FIG. 8. The respective mitral valves 49 and 50 are formed by securing a flexible durable biocompatible complete premolded covering 51,52 respectively, to the covered stent 40. This provides two opposed, molded flexible, flapably-movable symmetric valve leaflets 53 and asymmetric valve leaflets 54, respectively along the smooth curve 55, 56 defining the upper perimeter of the reliefs. The valve leaflets are each preformed and molded to the configuration shown in FIGS. 5A, 5B and 5C (for the symmetric valve leaflets) and in FIGS. 6A, 6B and 6C (for the asymmetric valve leaflets). These figures show the leaflets (53,54) the posts (42) and the reliefs (43) as well as the smooth curve (55,56) defining the upper perimeter of the reliefs (43). Thus, the valve leaflets are preformed and molded so that the free marginal edges of the valve leaflets along the free edge of each of the leaflets between the tips of the struts is related to the circumference of the circular base 11 in the following predetermined manner. When the valve is in the open position, the cross-sectional area is substantially equal to the crosssectional area of the inside of the circular base 44. When the valve is in its relaxed and natural closed position, the free edges of the leaflets 53,54 drop down and sealing meet in substantially wrinkle-free form at a curve of apposition (55,56) in the plane defined by the tips 44 of the struts 42 and the axis of the valve. The shape of the leaflets, as computed above and shown in FIGS. 2, or 3 respectively were molded in a manner to be described hereinafter.

In the embodiment of this invention as shown in FIGS. 10 and 11, the mitral valve 49 in its closed position has two equal leaflets 53 which form a line of apposition 55 in the plane defined by the tip 41 of each stent strut 42 of the stent and the axis of symmetry of the valve 49, and which approximates that of the surface formed by two coapting symmetrical bubbles under pressure. In the open position, the valve 49 provides an approximately cylindrical shape of the tissue with an exit area equal to the inside area of the cylindrical member or circular base 44 of the stent 40.

In the embodiment shown in FIGS. 10 and 11, the length of tissue between the tips 41 of each stent strut 42 in the closed position equals half the circumference of the exit aperture of the valve 49. This is achieved by having a curved dropped closure line from the strut tips 41 towards the cylindrical base member or ring 44.

In the embodiment of this invention as shown in FIGS. 12 and 13, the mitral valve 50 in its closed position has two unequal leaflets 54 which form a curve of apposition 56 in the plane defined by the tip 41 of each stent strut 42 and the axis of symmetry of the valve 50, and which approximates that of the surface formed by two coapting asymmetrical bubbles under pressure. In the open position, the valve 50 provides an approximately cylindrical shape of tissue with an exit area equal to the inside area of the cylindrical member or circular base 44 of the stent 40.

Bovine pericardium was selected as the material for construction of the valve leaflets since, when treated with glutaraldehyde, it has acceptable durability and biocompatibility. Other naturally-occurring materials. e.g. bovine, porcine, human (pericardium, fascia lata, dura mater) or synthetic materials, e.g. polyurethanes e.g. that known by the Trade Mark of AVOTHANE of acceptable durability and biocompatibility may also be used. A flexible stent made of acetal copolymer, is preferably used since it allows flexibility and thereby provides greater valve durability.

(v) Description of Prototype Valve

A prototype valve of one embodiment of this invention was fabricated as follows:

The stent may be made from a synthetic plastics material known by the Trade Mark DELRIN (duPont) by first matching a hollow cone with a vertex angle of approximately five degrees or a hollow cylinder. The machined plastic was cut by two planes each at approximately forty-five degrees to the vertical axis to give the stent configuration shown in FIG. 4. The plastic stent is slightly flexible, so that it may absorb some of the load applied on the leaflets when the valve is closing.

Small holes 60 were drilled around the base of the ring 44 of the stent 40 and at the edges of the stent 40, on the vertical posts 42 and at the tips 41 of the stent posts 42 through which sutures would be passed to attached the tissue leaflets.

Using the shape of each leaflet computed as previously described, an inverse mould was constructed from acrylic plastic cross-sections. The outline of these sections was computer generated directly from the bubble data. From the array of surface data points, a series of cross-sections parallel to the vertical plane through the stent posts were generated. Where necessary, additional points were interpolated to the grid used to compute the bubble surface. An inverse mould was then machined using a photograph machine. The mold used to form the valve leaflets was cast using silicone rubber in the inverse mould.

Figure 14:
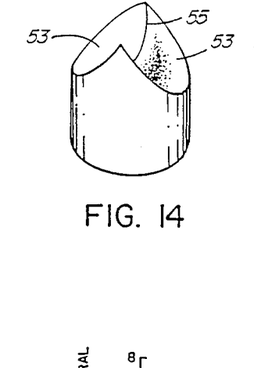
FIG. 14 is a perspective view of a mold for forming the two leaflets of the symmetric mitral valve of one embodiment of this invention.
Figure 15:
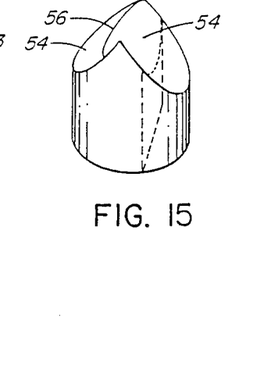
FIG. 15 is a perspective view of a mold for forming the two leaflets of the asymmetric mitral valve of one embodiment of this invention.

Two separate silicone rubber concave moulds (one per leaflet) were obtained from this original through a series of intermediate casts as seen in FIGS. 14 and 15. Fresh bovine pericardium of approximately uniform thickness was formed over each mould and was then partially fixed in 0.625% buffered glutaraldehyde solution for 30 to 40 minutes. The shaped pericardium leaflets were then removed from the moulds and re-immersed in glutaraldehyde for an additional 24 hours for complete fixation. The preformed leaflets were trimmed and placed on the stent, along with the suturing annulus (See FIGS. 7 and 8). The leaflets and annulus were secured using sutures through the holes in the stent. It is recognized that pericardium is not absolutely homogeneous and isotropic and that under physiologic loading the leaflets may distort from the intented bubble shape. Therefore material was selected as uniform as possible so that the tensile stresses in the bubble valve leaflets under pressure may be as evenly distributed as possible. The fixed and preformed leaflets were trimmed and attached to the stent using sutures through the holes in the stent.

The closed configuration of the new valve, hereafter referred to as the bubble valve (BV), is depicted in FIGS. 11 and 13.

OPERATION OF PREFERRED EMBODIMENT (i) Test Apparatus

The performance of the valve was measured in an apparatus which provided a hydromechanical simulation of the left heart system and peripheral circulation. It consists of an electric motor driven piston arrangement which hydraulically controls the volume of a flexible ventricle. The ventricle intakes a blood analogue fluid from a reservoir (atrium) through the mitral valve and pumps it through the aortic valve into a compliant aorta and physiological after-load and then back into the atrium. Pressure ports in the aorta, ventricle and atrium allow monitoring of the transvalvular pressure gradients. Flow rate through the mitral valve is measured directly by an electromagnetic flow transducer placed above it; the net flow rate in and out of the ventricle is obtained by electronically differentiating the output of the pistons's linear displacement transducer (which is proportional to the ventricle volume).

Figure 16:
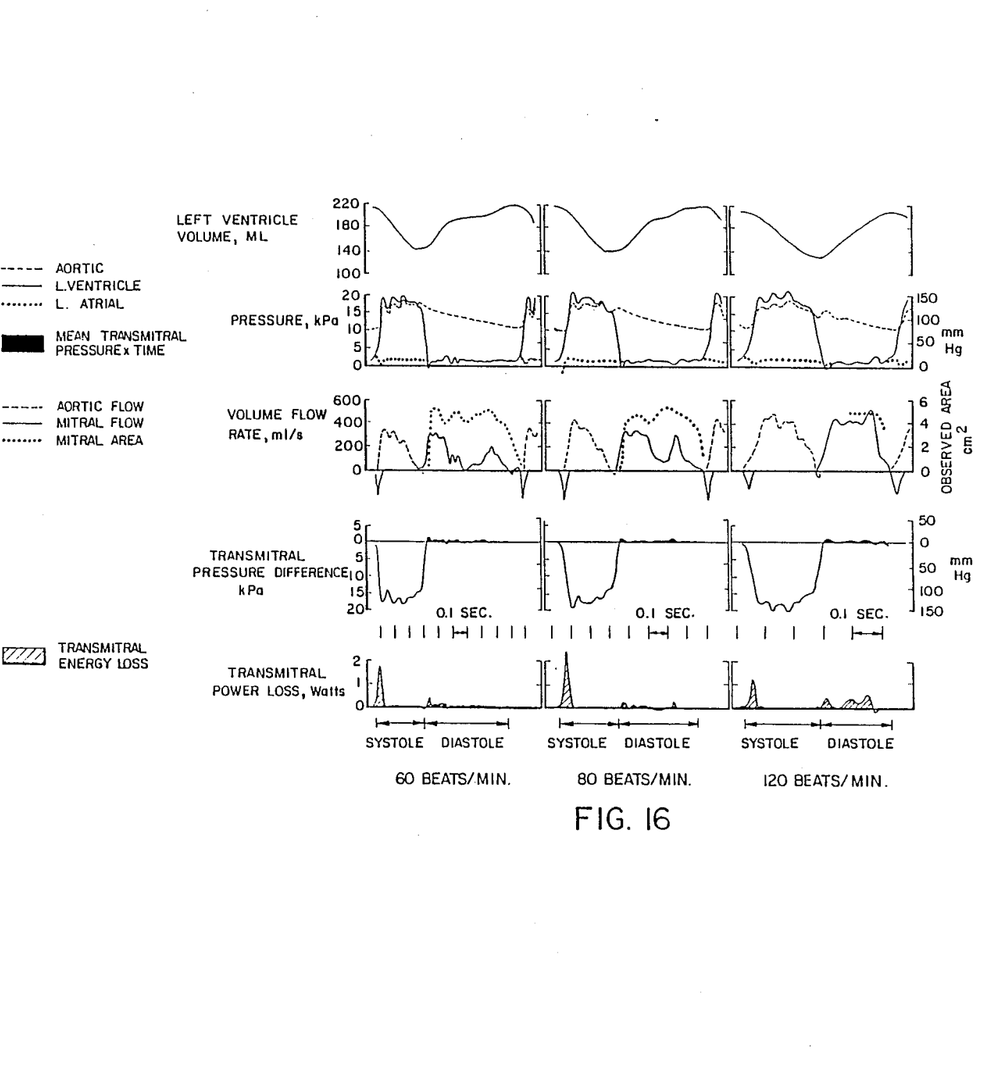
FIG. 16 is a series of graphs showing the waveforms for the bubble valve of aspects of this invention operating at three different heart rates, in vitro.

(ii) Description of FIG. 16

Ventricle volume, pressure, flow, observed valve area, and power loss waveforms for the bubble valve operating at 60, 80 and 120 beats per minute are shown in FIG. 16.

There are several different measures of the performance of a heart valve. The hydrodynamic performance of the bubble valve (BV) was compared with the Bjork-Shiley convexo-concave tilting disc valve (BSC) which exhibits small mean and maximum transvalvular pressure with the major orifice of the (BSC) valve oriented posteriorly (P). The Ionescu-Shiley three leaflet pericardial xenograph (IS) exhibits small total transvalvular energy loss, small regurgitation, and large observed open area. The results which follow compare the bubble valve (BV) with these two valves.

Figure 17:
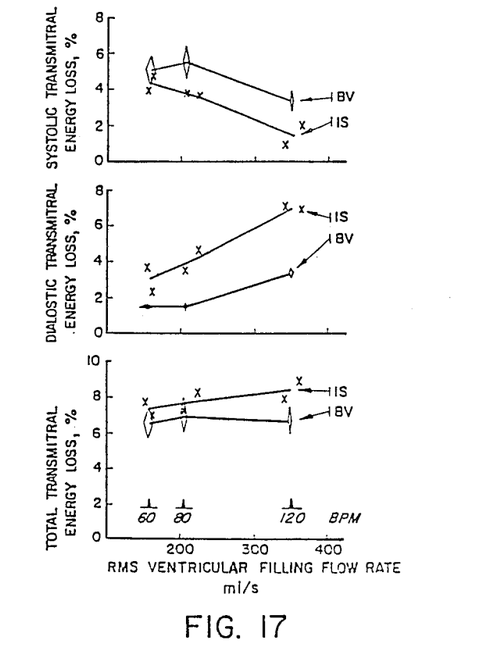
FIG. 17 (appearing on the same sheet as FIGS. 14 and 15) is a series of graphs showing the mean and maximum transmitral pressure difference observed area for the bubble valve (BV) operating at three different heart rates, in vitro, compared with the Bjork-Shiley convex-o-concave (BSC) operating in the posterior (P) orientation and the Ionescu-Shiley valve (IS). The reference orifice (RO) pressure difference for a valveless 29 mm diameter opening is also shown.

(iii) Description of FIG. 17

The mean and maximum transvalvular pressures across the bubble valve (BV) and the Bjork-Shiley (BSC) valve at three heart rates are shown in the top section of FIG. 17. It can be seen that the bubble valve shows marginally better performance at all heart rates. The pressure across the mitral orifice with no valve in the mitral position has also been shown in order to indicate the pressure drop caused by a reference orifice (RO) having an area corresponding to a tissue annulus diameter of 29 mm.

The maximum observed area for the bubble valve (BV) and for the Ionescu-Shiley (IS) valve are shown in the bottom section of FIG. 17. It can be seen that at all heart rates the bubble valve area is approximately 60% larger than that of the Ionescu-Shiley valve, and that it equals the primary orifice area of the stent (shown by the dashed line).

Figure 18:
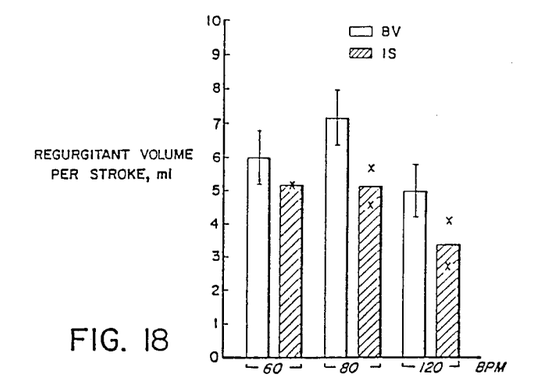
FIG. 18 is a bar graph showing the regurgitation for the bubble valve (BV) of aspects of this invention and two Ionescu-Shiley valves (IS) at three different heart rates, in vitro.

(iv) Description of FIG. 18

A normalized are of 1.0 shown in FIG. 18, is the area (6.6 sq.cm.) corresponding to a tissue annulus diameter of 29 mm.

FIG. 18 shows the regurgitant volume for the bubble valve (BV) and for the Ionescu-Shiley (IS). Since competent tissue valves seal absolutely this regurgitant volume is due entirely to fluid passing retrograde through the valve while it is closing. The fact that the leaflets of the bubble valve move a greater distance than those of the Ionescu-Shiley valve in going from the fully open to the closed position probable explains the slightly larger regurgitant volume for the bubble valve. The error for the bubble valve show the standard deviation for six different cycles. The data points for the Ionescu-Shiley valve show the regurgitant volumes measured for two different valves.

Figure 19:
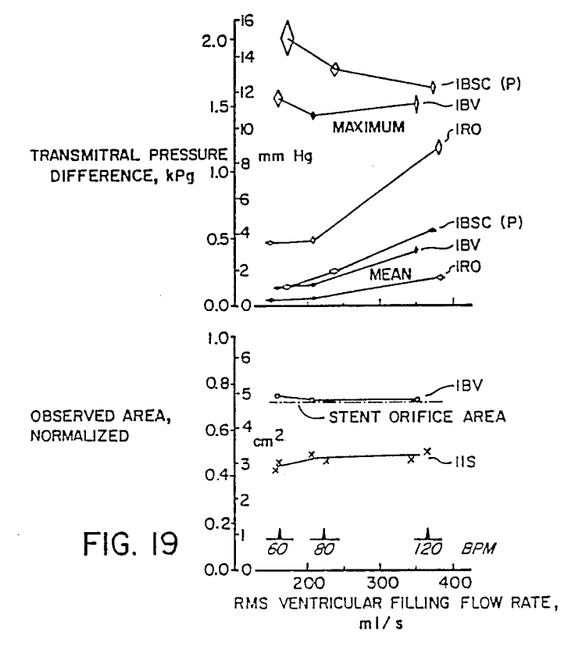
FIG. 19 is a series of graphs showing the systolic, diastolic and total transmitral energy loss for the bubble valve (BV) and two Ionescu-Shiley (IS) valves operating at three different heart rates in vitro. The rhombi show the standard deviation of the energy loss over six cycles for the bubble valve. The energy values for the Ionescu-Shiley valve are marked with an "X".

(v) Description of FIG. 19

It is preferred to use transvalvular energy loss when comparing valves since it gives an integrated measure of performance throughout the entire cardiac cycle. It cannot be used clinically, however, and for this reason the generally used clinical measures of valve performance, namely, transvalvular pressure and regurgitation have been given. FIG. 19 shows the systolic (top section), diastolic (middle), and total transvalvular energy loss (bottom) for the bubble valve (BV) and for the Ionescu-Shiley (IS) at three heart rates. Although the bubble valve has greater systolic energy loss than the Ionescu-Shiley valve this is more than compensated for by a lesser diastolic loss so that the total energy loss of the bubble valve is less than that of the Ionescu-Shiley valve.

For all the measures of performance reported here the bubble valve exceeds or nearly equals the best of the commercially available valves tested. The open area of the bubble valve has been optimized by having it open to the inside orifice area of the stent. A bubble surface is now used which is considered to be a more rational choice for the shape of the two leaflets of the valve in the closed position. By having two rather than three stent posts the possibility of perforation of the left ventricle wall has been considerably reduced. Since the systolic and diastolic transvalvular energy losses of the bubble valve are approximately equal at 120 beats per minute we conclude that further improvement of the bubble valve should be directed toward the systolic performance.

Tissues valves have the decided advantage that they are considerably less thrombogenic than mechanical types. Another important performance criterion for a heart valve however is its durability. The bubble valve was designed so that the stresses in the closed leaflet would be evenly distributed. The use of two rather than three leaflets does mean however that the flexing of the leaflets is greater than for a three leaflet valve.

SUMMARY

In summary, based on the measurements of the transvalvular pressure, open area, regurgitation, and transvalvular energy loss of the valve, the performance exceeds or nearly equals that of the best of the commercially available valves. Moreover such fatuque tests as have been conducted to date on 29 mm size valves has proved to be equivalent to approximately 6 years of wear-free and failure free performance. Two valves have been implanted in animals at the Mayo Clinic, and this study is ongoing.

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

We claim:

1. A mitral heart valve comprising: a stent including a circular base and a pair of upstanding struts separating a pair of arcuately-shaped, depressed, reliefs, each said relief being bounded by a smooth curve interconnecting said struts to said circular base; a flexible, durable, biocompatible covering secured to said stent and providing two opposed, moulded, flexible, flappably-movable valve leaflets secured along a smooth curve defining the upper perimeter of the reliefs; said valve leaflets each being preformed and moulded so that the free margin of said biocompatible leaflets along the free edge of each of said leaflets between the tips of said struts is related to the circumference of said circular base such that, when said valve is in its open position, the cross-sectional area is substantially equal to the cross-sectional area of the inside of said circular base, and when said valve is in its relaxed and natural position, the free edges of said leaflets drop down and sealingly meet in substantially wrinkle-free form at a curve of apposition, the shape of said leaflets in that closed position approximating that of a surface formed by two coapting bubbles under pressure, the shape of said surface formed by said two coapting bubbles under pressure being defined by the following five simultaneous equations:

$$S(u) = 2 \int_D \int \sqrt{1 + u_x^2 + u_y^2} \, dx \, dy + \oint_{\partial D} u(x,y) \, d\sigma \quad (1)$$

$$I(u) = 2 \int_D \int \sqrt{1 + u_x^2 + u_y^2} \, dx \, dy + \oint_D u(x,y) \, d\sigma + \lambda \int_D \int u(x,y) \, dx \, dy \quad (2)$$

$$\frac{\partial}{\partial x} \left[ \frac{u_x}{\sqrt{1 + u_x^2 + u_y^2}} \right] +$$

$$\frac{\partial}{\partial y} \left[ \frac{u_y}{\sqrt{1 + u_x^2 + u_y^2}} \right] = 2\lambda \quad (3)$$

$$3 u_y^2 = 1 + u_x^2 \text{ at } x = 0. \quad (4)$$

$$u(x,y) = x \sin\alpha \; x,y \in D. \quad (5)$$

wherein:

$$u_x = \partial \frac{du}{dx} \; ; \text{ and } u_y = \partial \frac{du}{dy} \; ;$$

α is the angle between the plane containing the stent boundry and x-y plane; and D is an ellipse having a short side "a" and a long side "b" formed as a projection of the stent boundry in the x-y plane.

2. The mitral heart valve of claim 1 wherein said curve of apposition is in the plane defined by the tip of said struts and the axis of said valve.

3. The mitral heart valve of claim 2 wherein the free edges of said leaflets meet at a curve which follows the shape of a catenary.

4. The mitral heart valve of claim 2 wherein said valve leaflets comprise two equal, identical, opposed, moulded, flexible, flappably-movable valve leaflets.

5. The mitral heart valve of claim 2 wherein said valve leaflets comprise two unequal, opposed, moulded, flexible, flappably-movable valve leaflets.

6. The mitral heart valve of claim 3 wherein said valve leaflets comprise two equal, identical, opposed, moulded, flexible, flappably-movable valve leaflets.

7. The mitral heart valve of claim 3 wherein said valve leaflets comprise two unequal, opposed, moulded, flexible, flappably-movable valve leaflets.

8. The mitral heart valve of claim 6 wherein said struts are substantially identical.

9. The mitral heart valve of claim 6 wherein said reliefs are symmetrically disposed equidistant from said struts.

10. The mitral heart valve of claim 7 wherein said reliefs are asymmetrically disposed with respect to said struts.

11. The mitral heart valve of claim 6 wherein said struts lie within the surface of a cone having the circular stent base as the conic base.

12. The mitral heart valve of claim 7 wherein said struts lie within the surface of a cone having the circular stent base as the conic base.

13. The mitral heart valve of claim 6 wherein said leaflets are secured to each other and to said struts by sutures.

14. The mitral heart valve of claim 7 wherein said leaflets are secured to each other and to said struts by sutures.

15. The mitral heart valve of claim 6 wherein said smooth curve interconnecting said struts is a parabola.

16. The mitral heart valve of claim 7 wherein said smooth curve interconnecting said struts is a parabola.

17. The mitral heart valve of claim 6 wherein said stent is formed of a flexible, elastically-deformable material, so that said struts may flex slightly.

18. The mitral heart valve of claim 7 wherein said stent is formed of a flexible, elastically-deformable material, so that said struts may flex slightly.

19. The mitral heart valve of claim 17 wherein said material is polypropylene or an acetal copolymer.

20. The mitral heart valve of claim 18 wherein said material is polypropylene or an acetal copolymer.

21. The mitral heart valve of claim 6 wherein said valve leaflets are formed of bovine, porcine or human fascia lata or dura mater, or of polyurethane.

22. The mitral heart valve of claim 7 wherein said valve leaflets are formed of bovine, porcine or human fascia lata or dura mater, or of polyurethane.

23. The mitral heart valve of claim 6 wherein said stent is covered with a pericardial covering.

24. The mitral heart valve of claim 7 wherein said stent is covered with a pericardial covering.

25. The mitral heart valve of claim 1 wherein the shape of said bubble surfaces is computed from the solution of said five equations simultaneously by discretizing said equations and solving by a numerical technique by dividing the ellipse into four pieces, forming a grid on half of D, discretizing the partial derivatives of second order finite difference approximations and solving the resulting non-linear algebraic equations by successive non-linear overrelaxation.

26. The mitral heart valve of claim 6 wherein the shape of said bubble surfaces is computed from the solution of said five equations by discretizing said equations and solving by a numerical technique by dividing the ellipse into four pieces, forming a grid on half of D, discretizing the partial derivatives of second order finite difference approximations and solving the resulting non-linear algebraic equations by successive non-linear overrelaxation.

27. The mitral heart valve of claim 7 wherein the shape of said bubble surfaces is computed from the solution of said five equations by discretizing said equations and solving by a numerical technique by dividing the ellipse into four pieces, forming a grid on half of D, discretizing the partial derivatives of second order finite difference approximations and solving the resulting non-linear algebraic equations by successive non-linear overrelaxation.

28. The mitral heart valve of claim 6 wherein said valve leaflets are formed of pericardium treated with glutaraldehyde.

29. The mitral heart valve of claim 7 wherein said valve leaflets are formed of pericardium treated with glutaraldehyde.

* * * * *